United States Patent [19]

Drobnik et al.

[11] 4,245,064

[45] Jan. 13, 1981

[54] ACTIVATED SOLID CARRIER AND A METHOD OF ITS PREPARATION

[75] Inventors: Jaroslav Drobník; Jaroslav Kalal; Jiří Labsky; Vladimír Saudek, all of Prague; František Švec, Kladno, all of Czechoslovakia

[73] Assignee: Ceskoslovenska akademie ved, Prague, Czechoslovakia

[21] Appl. No.: 11,428

[22] Filed: Feb. 12, 1979

[30] Foreign Application Priority Data

Feb. 22, 1978 [CS] Czechoslovakia .................. 1125/78

[51] Int. Cl.[3] ........................ C08F 8/18; C08C 19/12; C07H 13/02; C12N 11/10

[52] U.S. Cl. .................................... 525/329; 435/178; 435/179; 435/180; 435/181; 525/336; 525/359; 525/508; 536/119

[58] Field of Search ............... 525/359, 329, 336, 508; 435/178, 179, 180, 181; 536/119

[56] References Cited

U.S. PATENT DOCUMENTS

| | | | |
|---|---|---|---|
| 3,705,890 | 12/1972 | Barker et al. | 435/179 |
| 3,879,353 | 4/1975 | Crawford | 525/359 |
| 3,959,078 | 5/1976 | Guire | 435/179 |
| 4,090,919 | 5/1978 | Chibata et al. | 435/178 |
| 4,101,721 | 7/1978 | Rich et al. | 525/359 |

*Primary Examiner*—William F. Hamrock

[57] ABSTRACT

The invention relates to a solid insoluble carrier which is activated for bonding of nucleophilic groups and to a method of its preparation. The carrier contains active groups —O.CO.O.R, where R is the residue selected from the group comprising nitrophenyl, dinitrophenyl, trichlorophenyl, pentachlorophenyl, N-succinimidyl, N-phthalimidyl, and 8-quinolinyl. Active groups are bonded to polysaccharides, phenol-formaldehyde resins, polyacrylates, or polyacrylamides. The invention further relates to a method for preparation of the polymeric carrier, which consists in treatment of polymers carrying hydroxyl functions and selected from the group comprising polysaccharides, phenol-formaldehyde resins, polyacrylates, and polyacrylamides, with esters of chloroformic acid which contain the above mentioned active groups.

4 Claims, No Drawings

ACTIVATED SOLID CARRIER AND A METHOD OF ITS PREPARATION

The invention relates to a solid insoluble carrier which is activated for bonding of nucleophilic groups and to a method of its preparation.

Recently, reagents are used, in numerous chemical and physico-chemical processes, which consist of a virtually inert particle - carrier, mostly of a polymeric character, insoluble in the employed system of solvents and carrying bonded substances (ligands) which provide the required specific effect. These ligands may be either natural or synthetic compounds and their specific effect is either catalysis or selective sorption. According to that, the resulting reagents belong to the group of immobilized enzymes or among immobilized affinants, as enzymes (for the sorption of inhibitors), inhibitors, antigens, antibodies, lectins, nucleic acids, and the like.

The preparation of these reagents is based on bonding of a specific ligand to the carrier. Th free amino group of ligands is most commonly used for this purpose, however, methods are also known for bonding by means of carboxyls, by coupling of suitable aromatic residues, or by sulfhydryl groups (Immobilized Enzymes, Ed. Ichiro Chibata, John Wiley, New York 1978 p. 15–49). The bonding may occur immediately to the activated carrier or a spacer is inserted between the carrier and the ligand. The carriers may be divided into two groups: Active carriers, carrying in their structure such groups, which are able to react with ligands practically spontaneously, and activable carriers, bonding groups which has to be previously activated for the reaction with ligands. If the activation results in the activated carrier which is atorable, we are dealing with the transformation of the inactive carrier to the active one. Such activation processes are most suitable for practice. The most common groups which can be activated are hydroxyls. They are present in all carriers based on polysaccharides (cellulose and its derivatives, dextrans, agarose, etc.), and also in several synthetic carriers based, e.g., on the copolymers of 2-hydroxyethyl methacrylate (Spheron) or phenol-formaldehyde condensates (Duclite). To activate the hydroxyl groups of carrier, their conversion into imidocarbonate by means of cyanogen bromide is used often (Methods in Enzymology, Volume 44, Ed. Kl. Moosbach, Academic Press 1976, p. 46–53). The hydrolysis of cyanogen bromide as well as the formation of an inreactive carbamate are the undesirable side reactions. A part of imidocarbonate forms cross-links, which is manifested, e.g., in turning agarose insoluble in boiling water. Another parasitic reaction is the hydrolysis of imidocarbonate to carbonate and further to the original matrix. These side reactions together with reactive and toxic products of the reagent hydrolysis (bromide, cyanide and cyanate) are the substantial disadvantages of the cyanogen bromide method and restrain its application in larger scale, particularly in industry. The activation of hydroxyls is also performed with titanium tetrachloride, cyanuric chloride, diepoxides, divinylsulfone, benzoquinone, or by oxidation with sodium periodate to aldehyde groups which bind the ligand directly or via a spacer, most frequently via acylhydrazide. To enhance the strength of bond in these cases, the formed complex is reduced by borohydride (cf. reviews in Methods in Enzymology, Ed. S. P. Colowick and N. O. Kaplan, Band 34 and 44).

Other methods employ the oxidation as far as to carboxyls which are activated by means of carbodiimide or are transformed to alkyl esters and these further to hydrazides and azides. Carboxylic groups on the carrier may be also converted into, so called, activated esters, e.g. by the reaction with di(p-nitrophenyl)sulfite. The esters formed in this way directly react with amino groups of ligands creating the amide bond. It has been also described the activation of hydroxyls on the carrier by the direct action of phosgene. Reactive chloroformiate groups are formed in this way. Cellulose is usually converted to its derivative which is then activated for immobilization. Thus, for example, carboxymethylcellulose (CM-cellulose) is esterified, the ester is converted to hydrazide and the bonding is completed by the azide method.

The bonding to CM-cellulose by means of isoxazolium salts, carbodiimides, and isocyanides was also described. Cellulose may also be treated with bromacetyl bromide and hydroxyls can be esterified in this way with the acyl of monobromoacetic acid, which then reacts easily with amino ligands or with thiols. To carry out the bonding by diazotizing, cellulose may be modified by 4-chloromethylnitrobenzene which is reduced, aftěr linkage, to the corresponding amino derivative capable of diazotizing and coupling.

The above mentioned methods and other less frequently employed methods of immobilization have various disadvantages. In some cases, it is the hazard of employed reagents (BrCN, bromoacetyl bromide, phosgene) which causes the method inapplicable in larger scales. In other cases, it is the high price (cyanuric chloride) or, often, rather low yields ($TiCl_4$, periodate oxidation, azide preparation from CM-cellulose, etc.) which prevent broader application of these methods in practice. Only some of the known activation methods afford the activated carrier which can be stored and distributed; most of them give the carriers where ligands have to be bonded immediately after activation (Methods in Enzymology, Volume 44, Ed. Kl. Moosbach, Academic Press 1976, p. 166–167).

In the present time, we have found that a suitable bonding capacity is provided by carriers based on polymers which carry in their side chains the groups —0.-CO.OR$_1$, where R$_1$ is the residue of an activated ester selected from the group which comprises 4-nitrophenyl, 2,4-dinitropheny, 2,4,6-trichlorophenyl, 2,4,5-trichlorophenyl, pentachlorophenyl, N-succinimidyl, N-phthalimidyl, and 8-quinolinyl. The invention also relates to the method for preparation of the aforesaid carrier, wherein insoluble carriers containing hydroxyl groups are treated in an anhydrous medium with the activated ester of chloroformic acid of the general formula $ClCOOR_1$, where R$_1$ is a residue selected from the group comprising 4-nitrophenyl, 2,4-dinitrophenyl, 2,4,6-trichlorophenyl, 2,4,5-trichlorophenyl, pentachlorophenyl, N-succinimidyl, N-phthalimidyl, and 8-quinolinyl, the unreacted ester of chloroformic acid and released hydrogen chloride are removed by washing, and the resulting product is used for the direct bonding of ligands or is reacted with a low-molecular-weight compound of the general formula $NH_2$—R$_2$, where R$_2$ is the residue of an alkyl ester of aliphatic acid or of an aromatic-aliphatic diamine and serves, in the known way, as a spacer.

The activated carrier is stable in the dry state and in non-aqueous solvents without limitation and relatively stable even in diluted aqueous solutions of acids (pH below 5.5). The activated carrier reacts in nonaqueous solvents and also in aqueous solutions with compounds which have free primary or secondary aliphatic amino groups or hydrazine groups.

The advantage of the activation according to this invention consists in the ready accessibility and a low price of the used activating reagents, common safety requirements for the work in chemical laboratory, stability of the resulting activated carrier, and high yields. Particularly advantageous is the activated carrier according to the invention in connection with the spacer introduced by the reaction of activated carrier with alkyl esters of ω-aminoacids, where alkyl is methyl, ethyl or propyl and where ω-aminoacid is advantageously 6-aminohexanoic acid, which is converted with hydrazine hydrate to the corresponding hydrazide. Hydrazine hydrate reliably removes the contingent unreacted activated esters on the one hand, and, on the other, the carrier prepared in this way bonds in high yields the compounds containing cytosine, especially nucleic acids. Another advantage is the possible occupation of unreacted hydrazides by glucose. To bond the compounds containing an amino group, hydrazide can be converted to azide in the known way.

Another advantageous application of the carrier according to the invention consists in the introduction of an interlink formed by aromatic-aliphatic diamine. In this case, the aliphatic amino group reacts with the activated ester of carbonic acid while the aromatic amine remains free for diazotizing or for bonding of carboxylic groups of a ligand, which are activated by carbodiimide. Carbodiimide activated carboxylic acids react with arylamines in higher yields than with alkylamines. Peptides and proteins, which should retain their amino groups, may be bonded by diazotizing and coupling. Diazotizing and coupling may be also used for bonding of nucleic acids.

The invention pertains to the carrier insoluble in common solvents and activated for bonding of nucleophilic groups, wherein the carrier contains, in its side chains, the groups —0.CO.OR$_1$, where the residue R$_1$ is selected from the group comprising 4-nitrophenyl, 2,4-dinitrophenyl, 2,4,6-trichlorophenyl, 2,4,5-trichlorophenyl, pentachlorophenyl, N-succinimidyl, N-phthalimidyl, and 8-quinolinyl, which react in an aqueous or nonaqueous medium with compounds containing a free primary or secondary aliphatic amine or hydrazine group, and wherein these compounds are either the required ligand or a spacer for bonding the ligand.

The invention also pertains to the method for preparation of the aforesaid activated insoluble carrier, wherein the insoluble carriers, selected from the group comprising polysaccharides, phenol-formaldehyde resins, polyacrylates, and polyacrylamides and carrying hydroxyl groups in their side chains, are treated in an anhydrous medium by an activated ester of chloroformic acid of the general formula ClCOOR$_1$, where R$_1$ is the residue selected from the group consisting 4-nitrophenyl, 2,4-dinitrophenyl, 2,4,6-trichlorophenyl, 2,4,5-trichlorophenyl, pentachlorophenyl, N-succinimidyl, N-phthalimidyl, 8-quinolinyl, the unreacted compounds and hydrogen chloride are removed by washing, and the resulting product is used for the direct bonding of ligands or is reacted with the low-molecular-weight compound of the general formula $NH_2$-R$_2$, where R$_2$ is the residue of an alkyl ester of aliphatic acid or of an aromatic-aliphatic diamine and serves as a spacer in the known way.

The following examples illustrate the invention without limiting its scope by any means.

EXAMPLE 1

Sepharose (5 ml; the bead form of agarose gel containing 4% of agarose. product of Pharmacia AB) was transferred into 1,4-dioxan, the solution was adjusted with dioxan to 10 ml, and 0.35 g of p-nitrophenyl chloroformiate was added. The suspension was shaken for 1.5 hour at room temperature and washed with 1,4-dioxan. 1,4-Dioxan was removed by suction and 5 ml of 0.05 M borate buffer of pH 8.2 m 25 mg of trypsin (57 units/mg), and 10 mg of $CaCl_2$ was added, and the mixture was shaken for 2 hours at 4° C. The preparation was washed with 0.5 M NaCl adjusted to pH 7.0 by 0.01 M phosphate buffer as long as it is not yellow-coloured after alkalization with carbonate and then with 0.5% Triton X100 (a condensation product of iso-octylphenoxypolyethoxyethanol and oxirane, product of BDH). The found activity was 71 u./ml.

EXAMPLE 2

Spherical cellulose, prepared according to the Czechoslovak Pat. No. 172,7640, (5 ml) was worked out in the same way as described in Example 1 with the distinction that the shaking with p-nitrophenyl chloroformiate in 1,4-dioxan was extended to 4 hours and the temperature increased to 60° C. Nitrophenol was bonded in the amount of 0.136 mequiv./ml and the resulting activity of immobilized trypsin was 102 u./ml.

EXAMPLE 3 p-Nitrophenyl chloroformiate was bonded to 5 ml of spherical cellulose, prepared according to the Czechoslovak Pat. No. 172,640, (corresponding to U.S. Pat. No. 4,055,510) in the same way as in Example 2 and, after washing with 1,4.dioxan, 10 ml of 1,4-dioxan containing 0.3 g of ethyl 6-aminohexanoate hydrochloride and 0.39 ml of triethylamine was added. The suspension was shaken for 1 hour, washed with water, overcast with 5 ml of 80% hydrazine hydrate, allowed to stand for 16 hours at 60° C., and washed. The preparation contained 0.018 mequiv./ml of 6-aminohexanhydrazide.

EXAMPLE 4

The preparation obtained by the method described in Example 3 was shaken for 10 minutes at 4° C. with 5 ml of 1 M HCl and 0.1 g of $NaNO_2$, filtered off, washed with ice-cold water and 50 ml of ice-cold borate buffer in the same way as in Example 1. The found activity was 186 u./ml.

EXAMPLE 5 p-Nitrophenyl chloroformiate was bonded to 5 ml of spherical cellulose as in Example 2 and, after washing with 1,4-dioxan, the carrier was overcast with 5 ml of 80% hydrazine hydrate, shaken for 1 hour at room temperature, and washed with water. Hydrazine was bonded in the amount of 0.01 mequiv./ml.

EXAMPLE 6

The product from Example 5 was worked out to azide by the procedure described in Example 4. The found activity of bonded trypsin was 6 u./ml.

EXAMPLE 7

Spheron P-1000 (1 g; the macroporous bead copolymer of 2-hydroxyethyl methacrylate and ethylene dimethacrylate of particle size 20–40 μm; product of Lachema, Brno) was worked out by the procedure described in Example 3 and 4. The found activity of trypsin was 123 u./ml.

EXAMPLE 8

The macroporous spherical copolymer of glycidyl methacrylate with ethylene dimethacrylate (1 g; see F. Švec et al.: Angew. Makromol. Chemie 1977, 63, 23) was converted into the hydroxyl from by hydrolysis in 0.25 M $H_2SO_4$ (3 h, 80° C.), washed, and worked out by the procedure described in Examples 3 and 4. The found activity of trypsin was 51 u./ml.

EXAMPLE 9

Using the procedure described in Example 7, 125 mg of penicillin amidase (e.c. 3.5.1.11) of specific activity 3.5 u./mg was bonded to Spheron P-1000, with the distinction that 10 mg of $CaCl_2$ was omitted. The found activity of the resulting product was 40 u./ml.

EXAMPLE 10 p-Nitrophenyl chloroformiate was bonded to 5 ml of Sepharose CL-4 B in the same way as in Example 1 and, after washing with 1,4-dioxan, 10 ml of 1,4-dioxan containing 1.5 g of 1,6-diaminohexane was added. The suspension was shaken for 1 hour at room temperature and then washed with water. Diamine was bonded in the amount of 0.008 mequiv./ml. The product was shaken in 10 ml of 0.1 M phosphate buffer of pH 7 which contained 10 mg of $CaCl_2$ and 25 mg of trypsin, shaken for 4 hours at room temperature, and washed as described in Example 1. The found activity was 47 u./ml.

EXAMPLE 11

Analogously to Example 9, 125 mg of penicillin amidase was used in the procedure described in Example 10, with the distinction that $CaCl_2$ was omitted; 25 u./ml was bonded.

EXAMPLE 12

In the procedure identical with Example 1, 0.3 g of N-hydroxysuccinimide ester of chloroformic acid was used instead of p-nitrophenyl chloroformiate. The found activity was 83 u./ml.

EXAMPLE 13

In the procedure identical with Example 1, 0.5 g of 8-hydroxyquinoline ester of chloroformic acid was used instead of p-nitrophenyl chloroformiate. The found activity was 54 u./ml.

EXAMPLE 14

In the procedure identical with Example 1, pentachlorophenyl chloroformiate was used instead of p-nitrophenyl chloroformiate. The found activity was 35 u./ml.

EXAMPLE 15

In the procedure identical with Example 1, 2,4,5-trichlorophenyl chloroformiate was used instead of p-nitrophenyl chloroformiate. The found activity was 73 u./ml.

EXAMPLE 16

In the procedure identical with Example 1, 2,4,6-trichlorophenyl chloroformiate was used instead of p-nitrophenyl chloroformiate. The found activity was 40 u./ml.

EXAMPLE 17

In the procedure identical with Example 1, N-hydroxyphthalimide ester of chloroformic acid was used instead of p-nitrophenyl chloroformiate. The found activity was 65 u./ml.

EXAMPLE 18

In the procedure identical with Example 1, 2,4-dinitrophenyl chloroformiate was used instead of p-nitrophenyl chloroformiate. The found activity was 85 u./ml.

EXAMPLE 19 p-Nitrophenyl chloroformiate was bonded to 5 ml of Spheron 1000, similarly as in Example 2, by shaking for 4 hours. After washing with 1,4-dioxan, 10 ml of 1,4-dioxan containing 1.5 g of 4-amino(2-aminoethyl)benzamide hydrochloride and 0.55 ml (100 %) of triethylamine was added, shaken for 1 hour, and washed with water. Arylamine (4-aminobenzamide) was bonded in the amount of 0.01 mequiv./ml.

EXAMPLE 20

The product from Example 19 was worked out as described in Example 4, with the distinction that the saturated solution of $NaHCO_3$ in ice-cold water was used instead of the borate buffer. The found acivity of bonded trypsin was 54 u./ml.

EXAMPLE 21

The product from Example 19 was suspended in 10 ml of ice-cold water and pH was adjusted to 5.0. Pencillin amidase (50 mg) was added similarly as in Example 9 and 740 mg of N-cyclohexyl-N-[2-(4-morpholinyl-)ethyl] carbodiimide methyl-p-toluenesulfonate was added in three portions under continuous cooling by ice. The starting pH value was maintained during the reaction by means of an automatic titrator under moderate stirring. The addition proceeded for 2 hours, cooling with ice was continued for another hour, and the reaction was finished by incubation at room temperature for another three hours. Washing was carried out in the same way as in Example 1. The found activity of immobilized enzyme was 20 u./ml.

EXAMPLE 22

The immobilized preparation obtained in Example 9 was mixed with the 25% solution of saccharose in the ratio 1:5 and freeze-dried. It was stored in a sealed ampoule for 1 month at room temperature and after that the activity was checked showing 93% of the original value.

EXAMPLE 23

The product from Example 3 was suspended in 10 ml of 0.2 M acetate buffer of pH 4.2 and 10 ml of the solution was added, which contained 1.7 mg of desoxyribonucleic acid (DNA) in 1 ml of 1 M NaCl. The mixture was shaken for 24 hours at 60° C. The suspension was then washed with 1 M NaCl and water, 10 ml of the acetate butter (pH 5) which contained 5% of glucose was added, the mixture was shaken for 2 hours at 60° C., and washed in the same way as previously. The preparation contained 12 mg DNA in 1 ml and gave the negative reaction on free hydrazides.

EXAMPLE 24

In the procedure described in Example 23, the solution of cytosine was employed in the amount of 8.9 mg per 1 ml of the used carrier, instead of the DNA solution. The amount of bonded cytosine was 0.7 mg per 1 ml of the preparation.

EXAMPLE 25

The specific antibody against rabbit gammaglobulin (immunoglobulin, IgG) was bonded to the spheric macroporous carrier analogously to Example 8; 25 mg of IgG was added per each gram of the activated carrier. The added protein was bonded in the amount of 85% and if resumed its immunologic activity, which fact was confirmed by bonding the corresponding antigen.

EXAMPLE 26

The product for Example 19 was worked out as in Example 20, with the distinction that the pancreatic inhibitor of trypsin was used instead of trypsin. The inhibitor was added to the activated carrier in the amount of 15 mg/g. The polypeptide was bonded in the amount of 6% and was used in the affinity refining of trypsin.

EXAMPLE 27

Spherical cellulose prepared according to the Czechoslovak Pat. No. 172,640 (corresponding to U.S. Pat. No. 4,055,510) (5 ml) was activated in the same way as in Example 2 and, after activation, a solution containing 25 mg of concanavalin A in 5 ml was added instead of the trypsin solution. The resulting preparation was packed into a column and a calf serum was applied on the top of column. After thorough washing of the column, the bonded glycoproteins were liberated by glucose solution. Total amount of glycoproteins liberated from the applied 5 ml of serum preparation was 11.5 mg.

EXAMPLE 28

Sorbent Duolite S30 (5 ml; a macroporous phenol-formaldehyde polymer, product of Diamond-Shamrock) was worked out in the way described in Example 2. IThe found activity was 68 u./ml.

EXAMPLE 29

The solid phenol-formaldehyde carrier "Duolite Enzyme Support" (5 ml) product of Diamond-Shamrock) was worked out in the way described in Example 2, with the distinction that penicillin amidase characterized in Example 9 was added instead of trypsin, without addition of $CaCl_2$ at the same time. The found activity of resulting product was 34 u./ml.

EXAMPLE 30

Solid poly [N-(2-hydroxypropyl)methacrylamide] crosslinked with ethylene dimethyacrylate (5 ml) was worked out in the same way as described in Example 7. Further procedure was analogous to Examples 3 and 4. The final activity of bonded trypsin was 62 u./ml.

We claim:

1. A polymeric carrier containing hydroxyl groups which have been activated for bonding of nucleophilic groups, wherein this carrier is selected from the group comprising polysaccharides, phenol-formaldehyde resins, polyacrylates, polymethacrylates and polyacrylamides contains active groups of the general formula I $$—O.CO.OR_1, \quad (I)$$

where $R_1$ is the residue selected from the group comprising 4-nitrophenyl, 2,4-dinitrophenyl, 2,4,6-trichlorophenyl, 2,4,5- trichlorophenyl, pentachlorophenyl, N-succinimidyl, N-phthalimidyl and 8-quinolinyl.

2. The polymeric carrier as set forth in claim 1, wherein the active groups of the general formula I are bonded to polysaccharides.

3. The polymeric carrier as set forth in claim 1, wherein the active groups of general formula I are bonded to polyacrylates, polymethacrylates of the general formula II or polyacrylamides

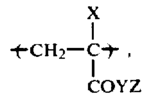

(II)

where X is hydrogen atom or $CH_3$, Y is —NH— or oxygen atom, and Z is mono- or dihyroxyalkyl, while alkyl contains 2 to 3 carbon atoms.

4. The polymeric carrier as set forth in claim 1, wherein said carrier is a polysaccharide and $R_1$ is 4-nitrophenyl.

* * * * *